United States Patent [19]

Angelucci et al.

[11] Patent Number: 4,891,360
[45] Date of Patent: Jan. 2, 1990

[54] 6-AMINO ANTHRACYCLINES, PROCESS FOR THEIR PREPARATION AND USE THEREOF

[75] Inventors: Francesco Angelucci, Milan; Mauro Gigli, Merano; Sergio Penco, Milan, all of Italy

[73] Assignee: Farmitalia Carlo Erba S.r.l., Milan, Italy

[21] Appl. No.: 73,109

[22] Filed: Jul. 14, 1987

[30] Foreign Application Priority Data

Jul. 21, 1986 [GB] United Kingdom ............... 8617742

[51] Int. Cl.$^4$ ..................... A61K 31/70; C07H 15/24
[52] U.S. Cl. ......................................... 514/34; 536/6.4
[58] Field of Search .......................... 536/6.4; 514/34

[56] References Cited

U.S. PATENT DOCUMENTS 4,348,388 9/1982 Garland et al. ................ 536/6.4

OTHER PUBLICATIONS

Morrison et al., *Organic Chemistry*, 3rd ed., 1979, p. 734.

*Primary Examiner*—Amelia Burgess Yarbrough
*Assistant Examiner*—Elli Peselev
*Attorney, Agent, or Firm*—Oblon, Spivak, McClelland, Maier & Neustadt

[57] ABSTRACT

Anthracycline glycosides having the general formula (A):

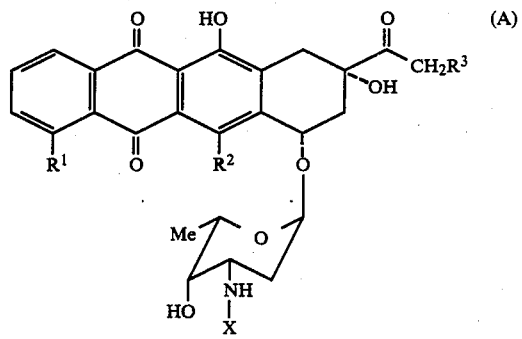

wherein $R_1$ is hydrogen, hydroxy or methoxy; $R_2$ is amino, $R_3$ is hydrogen or hydroxy and X is hydrogen; and their pharmaceutically acceptable salts; are antitumor agents. The compounds are obtained by reduction of the corresponding 6-nitro derivatives with stannous chloride in presence of sodium acetate or with palladium or charcoal in presence of cyclohexene.

18 Claims, No Drawings

6-AMINO ANTHRACYCLINES, PROCESS FOR THEIR PREPARATION AND USE THEREOF

The invention relates to novel anthracycline glycosides having antitumor activity, to methods for their preparation and to pharmaceutical composition containing them.

The present invention provides anthracycline glycosides of general formula (A):

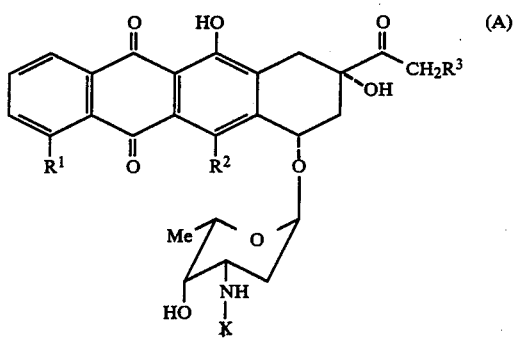

wherein R₁ is hydrogen, hydroxy or methoxy; R₂ is amino, R₃ is hydrogen or hydroxy; X is hydrogen; and pharmaceutically acceptable salts thereof.

The present invention also provides compounds, useful in the preparation of the glycosides of formula (A), of formula (2)

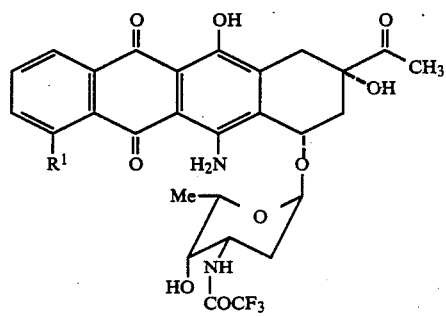

wherein R₁ is as defined above.

The invention therefore embraces a new class of anthracyclines of general formula (A') characterized by the following patterns of substitution:

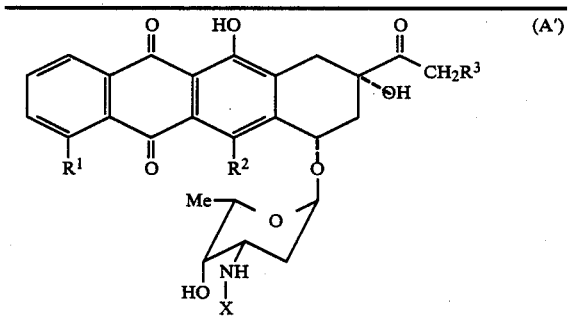

| Structure | Substitution | | |
|---|---|---|---|
| I | R¹ = R³ = H; | R² = NH₂; | X = COCF₃ |
| II | R¹ = R³ = X = H; | R² = NH₂; | |

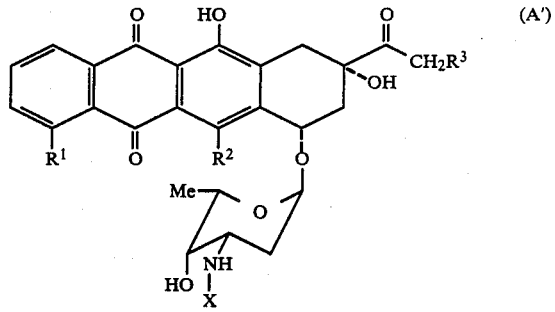

| Structure | Substitution | | |
|---|---|---|---|
| III | R¹ = X = H; | R² = NH₂; R³ = OH | |
| IV | R¹ = OH; | R² = NH₂, R³ = H; | X = COCF₃ |
| V | R¹ = OH; | R² = NH₂; R³ = X = H | |
| VI | R¹ = R³ = OH | R² = NH₂; | X = H |
| VII | R¹ = OCH₃; | R² = NH₂; R³ = H; | X = COCF₃ |
| VIII | R¹ = OCH₃; | R² = NH₂; R³ = X = H | |
| IX | R¹ = OCH₃; | R₂ = NH₂; R³ = OH; | X = H |

The pharmaceutically acceptable salts of the glycosides of formula (A) may be, for example, the hydrochloride salts.

The preparation of the new anthracycline glycosides is based on the direct reduction of nitro-anthracycline glycosides. It is well known that, under reducing conditions, the sugar moiety splits from anthracycline glycosides affording the 7-deoxy derivatives (F. Arcamone, Doxorubicin, Academic Press, 1981). However, it was found that the use of SnCl₂ in the presence of NaO-COCH₃ or of Pd/C in the presence of cyclohexene preserves the glycosidic linkage thus allowing the direct transformation of nitro-anthracycline glycosides to amino-anthracycline glycosides. Our approach, for synthesis of amino-anthracyclines, is therefore based on the use of 6-nitro anthracyclines of general formula (A') wherein R¹=H, OH, OCH₃; R²=NO₂; R³=H; X=COCF₃, described in our U.K. Application No. 8528440.

Accordingly, the present invention provides a process for the preparation of an anthracycline glycoside of the general formula (A) as defined above or a pharmaceutically acceptable salt thereof, which process comprises (i) treating an anthracycline glycoside of formula (1):

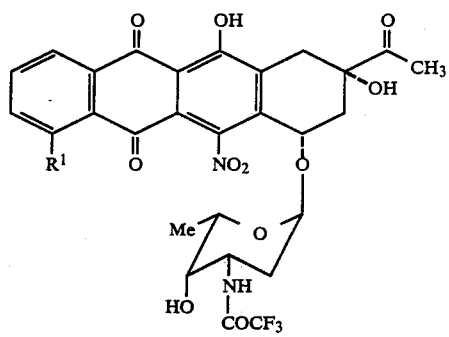

(1)

wherein $R_1$ is as defined above, with stannous chloride in presence of sodium acetate or with palladium on charcoal in presence of cyclohexene, to give the corresponding 6-deoxy-6-amino derivative of formula (2):

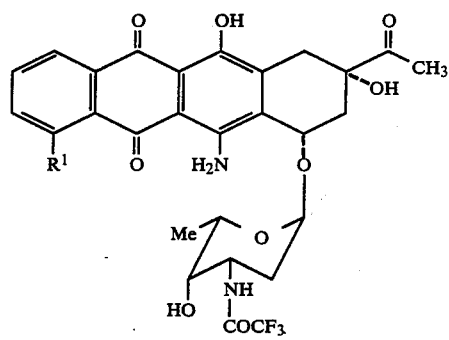

(2)

wherein $R_1$ as as defined above;

(ii) removing the N-trifluoroacetyl group from the compound of formula (2) so as to obtain a glycoside of formula (A) wherein $R_3$ represents a hydrogen atom;

(iii) if desired, converting the said glycoside of formula (A) into a pharmaceutically acceptable salt thereof;

(iv) if desired, brominating the said glycoside of formula (A) or pharmaceutically acceptable salt thereof and hydrolysing the 14-bromo derivative thus obtained so as to form the corresponding anthracycline glycoside of formula (A) wherein $R_3$ represents a hydroxy group; and (v) if desired, converting the said glycoside of formula (A) wherein $R_3$ represents a hydroxy group into a pharmaceutically acceptable salt thereof.

The first step in the process is shown in Scheme I below:

SCHEME I

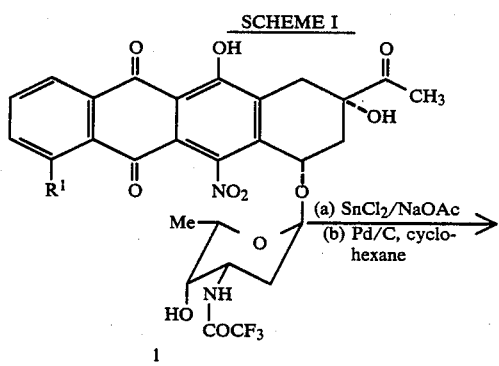

1

-continued
SCHEME I

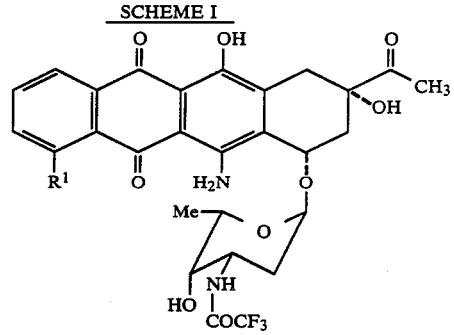

2 wherein $R^1$=H, OH, $OCH_3$.

By treating compound 1 (Scheme 1) with $SnCl_2$/NaOAc (method A) or alternatively with Pd/C and cyclohexene (method B), product 2 can be obtained in a very high yield (80%). After mild alkaline hyrolysis, in order to remove the N-trifluoroacetyl group, the daunorubicin analogs II, V, VII are obtained which may be converted to the corresponding doxorubicin analogs III, VI, IX, via bromination and treatment with sodium formate in accordance with the method described in U.S.-A-3803124.

Step (i) may be effected with the glycoside of formula (1) dissolved in methanol and at room temperature, with stirring and under a nitrogen atmosphere. Step (ii) may be carried out with an aqueous solution of sodium hydroxide, at 0° C., under a nitrogen atmosphere and with the glycoside of formula (2) being dissolved in acetone. Typically, step (iii) is effected by treating the said glycoside of formula (A) with a methanolic solution of hydrogen chloride and isolating the said glycoside of formula (A) as its hydrochloride. Step (iv) is generally effected by treating the said glycoside of formula (A) with a chloroformic solution of bromine and hydrolysing the 14-bromo derivative thus obtained with an aqueous solution of sodium formate. As for step (iii), step (v) is typically carried out by treating the said glycoside of formula (A) wherein $R_3$ represents a hydroxy group with a methanolic solution of hydrogen chloride and isolating the said glycoside of formula (A) wherein $R_3$ represents a hydroxy group as its hydrochloride.

The present invention also provides pharmaceutical compositions comprising an anthracycline glycoside of formula (A) or a pharmaceutically acceptable salt thereof, together with a pharmaceutically acceptable carrier or diluent. Conventional carries and diluents may be used. The composition may be formulated and administered in conventional manner. The compounds of formula (A) and their salts are useful in methods of treatment of the human or animal body by therapy. They are useful as antitumor agents by administering a therapeutically effective amount to a patient.

The invention is illustrated by the following Examples.

EXAMPLE 1

Preparation of 4-demethoxy-6-deoxy-6-amino-N-trifluoroacetyl daunorubicin (I)

Method A:

Product 1 ($R^1$=H) [0.16 g, 0.25 mM] was dissolved in MeOH (20 ml). NaOAc.3H$_2$O (0.8 g, 6 mM) in one pot and SnCl$_2$.H$_2$O (1.5 g, 6.6 mM) in 3 portions over a period of 90 min. were added at room temperature, nitrogen atmosphere and stirring. After 1 hour the solvent was removed in vacuo, the residue suspended with CH$_2$Cl$_2$ (100 ml) and treated with a satured aqueous solution of NaHCO$_3$ (50 ml) under stirring for 30 min.

After filtration over celite, the organic layer was separated, washed with H$_2$O until neutrality, dried over Na$_2$SO$_4$ and the solvent removed in vacuo. The residue was crystallized from diethyl ether to give I (0.125 g, yield 80%).

Method B:

Product 1 (R=H) [0.16 g, 0.25 mM] was dissolved in MeOH (20 ml). 0.1 g of Pd/C 10% and 2 ml of cyclohexene were added.

After refluxing for 10 min., the solvent was removed in vacuo and the residue crystallized from diethyl ether to give I (0.125 g, yield 80%). m.p.: 251°–252° C. (dec); I.R. (KBr): 3480, 3280, 3065, 1720, 1710, 1620, 1610, 1590, 1530 cm$^{-1}$; FC-MS: m/z 592 (M$^+$·); UV and visible spectra (MeOH)λmax: 202, 254, 290, 532, 566 nm; H$^1$-NMR (200 MHz, DMSO, T=50° C.) (inter alia). δ: 1.11 (d, J=6.4 Hz, 3H, 5'-CH$_3$), 2.25 (s, 3H, COCH$_3$), 5.02 (dd, J=3.9, 5.3 Hz, 1H, 7-H), 5.40 (d, J=2.9 Hz, 1H, 1'-H), 5.50 (s, 1H, 9-OH), 7.7–8.0 (m, 2H, 2-H, 3-H), 8.06 (broad, 2H, —NH$_2$), 8.2–8.3 (m, 2H, 1-H, 4-H), 8.91 (d, J=7.4 Hz, 1H, NHCOCF$_3$), 14.2 (1H, 11-OH).

EXAMPLE 2

Preparation of 4-demethoxy-6-deoxy-6-amino daunorubicin (II)

Product I (0.1 g, 0.168 mM) was dissolved in acetone (6 ml). The solution was cooled with ice and 0.1N NaOH (50 ml) was added with stirring and nitrogen atmosphere.

After 1 hour the pH was lowered to 4.5 with 0.1 N HCl and the solution extracted with CH$_2$Cl$_2$. The aqueous layer was adjusted again at pH 8 with 0.1N NaOH and extracted with CH$_2$Cl$_2$. The organic solution, washed with H$_2$O, was dried over Na$_2$SO$_4$ and the solvent removed in vacuo.

The residue, dissolved with MeOH (3 ml) was acidified with some drops of MeOH/HCl solution and the hydrochloride precipitated with diethyl ether. After filtration and washing with diethyl ether product II (0.08 g, yield 80%) was obtained.

FD-MS: 496 (M$^+$·), I.R. (KBr): 1710, 1620, 1610, 1585, 1520 cm$^{-1}$; U.V. and visible spectra (MeOH)-λmax: 202, 254, 290, 532, 566 nm.

EXAMPLE 3

Preparation of 4-demethoxy-6-deoxy-6-amino doxorubicin (III)

Following the method described in U.S.-A-3803124, bromination of 4-demethoxy-6-deoxy-6-amino daunorubicin (II) and subsequent hydrolysis of the obtained 14-bromo derivative with sodium formate, the title compound was obtained.

FD-MS: 512 (M$^+$); U.V.(KBr): 1710, 1620, 1610, 1585, 1520 cm$^{-1}$ U.V. and visible spectra (MeOH) max: 202, 251, 290, 532, 566 nm; TLC (Silica gel plate; eluent CH$_2$Cl$_2$/MeOH/CH$_3$COOH/H$_2$O 80:20:7:3) Rf: 0.38.

BIOLOGICAL ACTIVITY OF COMPOUND II AND COMPOUND III

Compound II (4-demethoxy-6-deoxy-6-aminodaunorubicin) and Compound III (4-demethoxy-6-deoxy-6-aminodoxorubicin) have been tested "in vitro" against Human Colon Adenocarcinoma Cell Line sensitive to doxorubicin (LoVo) and resistant to doxorubicin (LoVo/DX) in comparison with daunorubicin (DNR) and doxorubicin (DX).

The obtained results are reported in Table 1 and 2.

TABLE 1

In Vitro cytotoxicity (a) on human colon adenocarcinoma cell line sensitive (LoVo) and resistant to doxorubicin (LoVo/DX) of 4-demethoxy-6-deoxy-6-amino DNR

| | (b) ID$_{50}$ ng/ml | |
|---|---|---|
| | LoVo | LoVo/DX |
| COMPOUND II | 90 | 4400 |
| DNR | 42 | 2357 |

(a)Colony inhibition test: 4 hours treatment
(b)dose which gives 50% reduction of cell number in comparison with untreated controls

TABLE 2

In Vitro cytotoxicity (a) on human colon adenocarcinoma cell line sensitive (LoVo) and resistant to doxorubicin (LoVo/DX) of 4-demethoxy-6-deoxy-6-amino DX

| | (b) ID$_{50}$ ng/ml | |
|---|---|---|
| | LoVo | LoVo/DX |
| COMPOUND III | 99 | 1150 |
| DX | 26.6 | 833 |

(a)Colony inhibition test: —24 hours treatment
(b)dose which gives 50% reduction of cell number in comparison with untreated controls

I claim:

1. An anthracycline glycoside of formula (A):

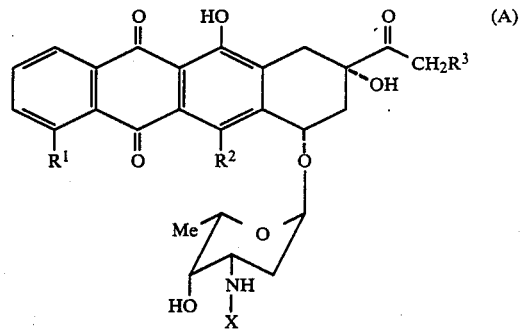

wherein $R_1$ is hydrogen, hydroxy or methoxy; $R_2$ is amino, $R_3$ is hydrogen or hydroxy; X is hydrogen; and pharmaceutically acceptable salts thereof.

2. A compound according to claim 1, wherein the anthracycline glycoside of formula (A) is 4-demethoxy-6-deoxy-6-amino daunorubicin.

3. A compound according to claim 1, wherein the anthracycline glycoside of formula (A) is 4-demethoxy-6-deoxy-6-amino doxorubicin.

4. A compound according to claim 1, wherein the anthracycline glycoside of formula (A) is 4-hydroxy-6-deoxy-6-amino daunorubicin.

5. A compound according to claim 1, wherein the anthracycline glycoside of formula (A) is 4-hydroxy-6-deoxy-6-amino doxorubicin.

6. A compound according to claim 1, wherein the anthracycline glycoside of formula (A) is 6-deoxy-6-amino daunorubicin.

7. A compound according to claim 1, wherein the anthracycline glycoside of formula (A) is 6-deoxy-6-amino doxorubicin.

8. An anthracycline glycoside of the formula

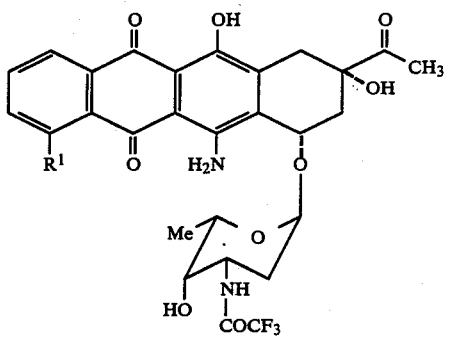

wherein $R^1$ is hydrogen, hydroxy or methoxy.

9. A process for the preparation of an anthracycline glycoside of the formula (A)

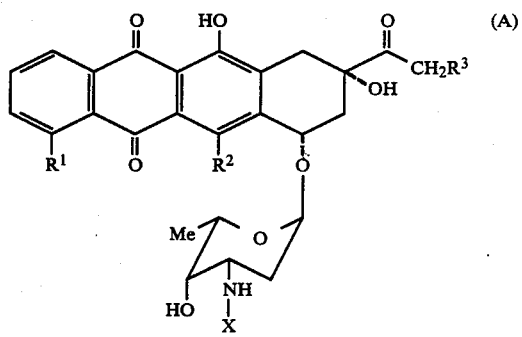

wherein $R_1$ is hydrogen, hydroxy or methoxy; $R_2$ is amino, $R_3$ is hydrogen or hydroxy; and X is hydrogen; or a pharmaceutically acceptable salt thereof, which process comprises (i) treating an anthracycline glycoside of formula (1):

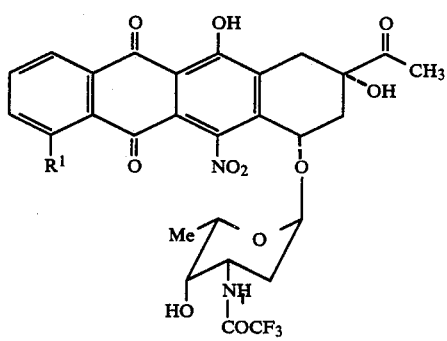

wherein $R_1$ is as defined in claim 1, with stannous chloride in presence of sodium acetate or with palladium on charcoal in presence of cyclohexene, to give the corresponding 6-deoxy-6-amino derivative of formula (2):

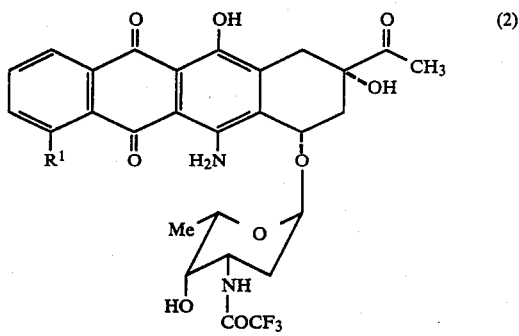

wherein $R_1$ is as defined above; and (ii) removing the N-trifluoroacetyl group from the compound of formula (2) so as to obtain a glycoside of formula (A) wherein $R_3$ represents a hydrogen atom.

10. A process according to claim 9, wherein step (i) is effected with the glycoside of formula (I) dissolved in methanol and at room temperature, with stirring and under a nitrogen atmosphere.

11. A process according to claim 9 or 10, further comprising (iii) converting the said glycoside of formula (A) into a pharmaceutically acceptable salt thereof.

12. A process according to claim 9 or 10, further comprising (iv) brominating the said glycoside of formula (A) or pharmaceutically acceptable salt thereof and hydrolysizing the 14-bromo derivative thus obtained so as to form the corresponding anthracycline glycoside of formula (A) wherein $R_3$ represents a hydroxy group.

13. A process according to claim 9 or 10, further comprising (v) converting the said glycoside of formula (A) wherein $R_3$ represents a hydroxy group into a pharmaceutically acceptable salt thereof.

14. A process according to claim 9 or 10, wherein step (ii) is effected with an aqueous solution of sodium hydroxide, at 0° C., under a nitrogen atmosphere and with the glycoside of formula (2) being dissolved in acetone.

15. A process according to claim 11, wherein step (iii) is effected by treating the said glycoside of formula (A) with a methanolic solution of hydrogen chloride and isolating the said glycoside of formula (A) as it hydrochloride.

16. A process according to claim 13, wherein step (iv) is effected by treating the said glycoside of formula (A) with a chloroformic solution of bromine and hydrolysing the 14-bromo derivatives thus obtained with an aqueous solution of sodium formate.

17. A process according to claim 13, wherein step (v) is effected by treating the said glycoside of formula (A) wherein $R_3$ represents a hydroxy group with a methanolic solution of hydrogen chloride and isolating the said glycoside of formula (A) wherein $R_3$ represents a hydroxy group as its hydrochloride.

18. A pharmaceutical composition having antitumor activity against colon adenocarcinoma comprising an effective amount of an anthracycline glycoside of formula (A) as defined in claim 1, or a pharmaceutically acceptable salt thereof, together with a pharmaceutically acceptable carrier or diluent.

* * * * *